United States Patent [19]

Kuczynski

[11] Patent Number: 5,490,942
[45] Date of Patent: Feb. 13, 1996

[54] PROCESS OF INHIBITING OXALATE SCALE FORMATION

[75] Inventor: Krzysztof Kuczynski, Rhode St. Genese, Belgium

[73] Assignee: Monsanto Company, St. Louis, Mo.

[21] Appl. No.: 257,855

[22] Filed: Jun. 10, 1994

[51] Int. Cl.$^6$ ..................................................... C02F 5/14
[52] U.S. Cl. ............................... 210/700; 162/48; 162/72; 162/199; 252/180
[58] Field of Search .................................... 210/698–701; 252/180; 162/48, 72, 73, 199

[56] References Cited

U.S. PATENT DOCUMENTS

| | | | |
|---|---|---|---|
| 3,619,427 | 11/1971 | Kautsky | 210/700 |
| 4,575,425 | 12/1984 | Boffardi et al. | 210/697 |
| 4,804,476 | 2/1989 | Sinkovitz et al. | 210/697 |
| 4,872,995 | 10/1989 | Chen et al. | 210/699 |
| 5,261,491 | 11/1993 | Stewart et al. | 210/700 |
| 5,338,477 | 8/1994 | Chen et al. | 252/180 |

FOREIGN PATENT DOCUMENTS

| | | |
|---|---|---|
| 0538026 | 4/1993 | European Pat. Off. . |
| 0479462 | 4/1994 | European Pat. Off. . |
| 2248830 | 4/1994 | United Kingdom . |

*Primary Examiner*—Peter A. Hruskoci
*Attorney, Agent, or Firm*—W. Brooks

[57] ABSTRACT

A process of inhibiting oxalate scale formation in aqueous systems is disclosed. A preferred class of scale inhibitors is represented by polyamino hexamethylene phosphonates. These phosphonate inhibitors can be used in levels of from 0.05 ppm to 300 ppm (of the aqueous solution) at pH in the near neutral to preferably alkaline medium.

6 Claims, No Drawings

PROCESS OF INHIBITING OXALATE SCALE FORMATION

This invention relates to a process of inhibiting scale formation and deposition, and more particularly to a method of inhibiting the formation of scale in aqueous systems which are primarily alkaline and contain oxalates.

Deposits of sparingly soluble calcium oxalate occur in industries and processes such as paper manufacture (especially in the pulping process), sugar beet processing, sugar clarification and whisky distillation.

Paper making processes are a major industry sector suffering from oxalate scaling because large volumes of water rich in calcium are used and because the wood, i;e. the basic raw material, is a natural source of oxalic acid (see "Handbook of Industrial Water Conditioning", sixth edition, third printing, Betz Laboratories Inc., Trevose, Pa. 19047, USA). The recirculation of process waters increases the concentration of oxalate and enhances further the tendency towards precipitation.

The undesirable effects of the deposition of oxalate scale are well documented in the literature-see J. A. Glazer— "Overview of Deposit Control", Tappi J., page 72 Jul. 1991.

Compounds which act as scale inhibitors, or mixtures of such compounds, do so by inhibiting the growth of crystals, thereby effecting a reduction in the formation of scale. Crystalline deposits can be effectively controlled by introducing an appropriate impurity into the crystal lattice. Such an impurity prevents further growth of the crystal and reduces or eliminates the scale formation. Phosphonates, polyphosphates and polymeric electrolytes are typically used for this purpose.

U.S. Pat. No. 4575425 describes a scale inhibiting formulation comprising water soluble phosphate, phosphonate or phosphinate and a water soluble polyelectrolyte.

U.S. Pat. No. 4804476 describes a scale inhibiting mixture comprising water soluble phosphates and polycarboxylates to inhibit the deposition of calcium oxalate in paper mills.

GB 2248830 and EP-A-0479462 describe methods useful in the oil industry for inhibiting the formation of scale in water having a high barium content and a low pH comprising the addition of an aqueous solution of defined polyaminomethylene phosphonates to the water to be treated.

Other substances used as typical scale inhibitors include sulphonated ethoxylated hydrocarbons, polyacrylates, and organic polyphosphonic acids. The "other" scale inhibitors are chemically different from the phosphonate compounds in accordance with claim 1 and can be represented by all compounds which are known to exhibit scale inhibiting and/or dispersing properties. Examples of the like "other" scale inhibitors include : phosphonates such as diethylenetriamine pentamethylene phosphonate, ethylenediamine tetramethylene phosphonate. Examples of non-phosphonate "other" scale inhibitors include homopolymeric and copolymeric, e.g. terpolymeric scale inhibitors such as homopolymers of acrylic acid and methacrylic acid and copolymers of acrylic and methacrylic acids, acrylic and 2-acrylamido-2-methyl propyl sulfonic acids, methacrylic and 2-acrylamido-2-methyl propyl sulfonic acids, acrylic acid and 2-hydroxypropyl acrylate and methacrylic acid and 2-hydroxypropyl acrylate.

It has now been found that, surprisingly, certain known polyaminomethylene phosphonates may be used as effective scale inhibitors in aqueous systems and solutions having a high oxalate content, which are only mildly acidic or are alkaline in character, and which contain, as do most commercially used waters, alkaline earth metal cations such as calcium.

According to the present invention there is provided a method for inhibiting the formation of calcium oxalate scale deposition in aqueous solutions which comprises adding to the aqueous solution a phosphonate compound having the formula:

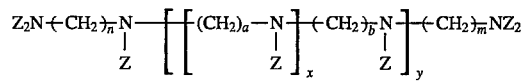

wherein $Z=-CHR^1PO_3R_2$ $R=H$, $CH_3$, $C_2H_5$ or M $R^1=H$, $CH_3$, $CR_3$, $C_6H_5$, $SO_3H_2$ M=alkali metal or ammonium ion n=2–6, preferably 2–4 m=2–6, preferably 2–4 a=2–10, preferably 2–4 b=2–10, preferably 2–6 x=0–6, preferably 0–3 y=1–6, preferably 1–2 in an amount of from 0.5 ppm to 300 ppm, expressed by reference to the aqueous solution, the aqueous solution having a pH at 20° C. of from 5 to 13.

The method herein is usually applied at a temperature in the range from 15° C. to 90° C. preferably from 25° C. to 70° C.

Preferably the phosphonate compound is one wherein, in the above formula, n=3, m=3, b=2, x=0, y=1, and R and R1 are H or M, i.e. the compound having the formula:

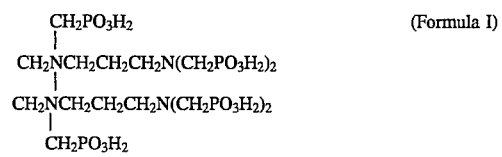

(Formula I)

The foregoing compounds are very efficient inhibitors of oxalate scale formation when applied alone, but may be used as an ingredient in other formulations which contain other scale inhibiting or adjuvant substances.

The method of the invention is particularly effective in aqueous systems having a pH of 6 and above, and are even more effective when used in aqueous systems where the pH is greater than 6. Preferably the pH is within the range of 7 to 13, and even more preferred is a pH range of 7 to 11.

Preferred amounts of the inhibiting agent used are in the range of 0.2 to 1000 ppm, for example from 0.5 to 300 ppm or 0.5 to 100 ppm and, more preferably, these are between 1 and 50 ppm.

The invention is illustrated by the following Example.

EXAMPLE 1

The preferred oxalate scale inhibiting compound of the invention, i.e. the compound of formula I above, was tested alongside various members of the known "DEQUEST" family of phosphonate inhibitors under conditions similar to those encountered in an alkaline pulp bleaching process. The word "DEQUEST" is a Registered Trade Mark.

The temperature of the aqueous solution used in the tests was maintained at 45° C. and the pH at 9.5 (adjusted using an ammonium hydroxide/ammonium chloride buffering agent). Tests times of 2.5, 8 and 24 hours were deployed, and concentrations of 100 ppm of calcium and 80 ppm of oxalates were present in the aqueous solution. A dosage rate of inhibitor of 25 ppm was used in each test. The results obtained are set out below in the Table. The "DEQUEST" scale inhibitors used in the tests were designated A to E and were as follows:

A—DEQUEST 2066
(diethylenetriaminepenta(methylenephosphonic acid) or its salts)

B—DEQUEST 2046
(ethylenediaminetetra(methylenephosphonic acid) or its salts)

C—DEQUEST 2000
(aminotri(methylenephosphonic acid) or its salts)

D—DEQUEST 2010
(1-hydroxyethylene(1,1 diphosphonic acid))

E—DEQUEST 2056
(hexamethylenediaminetetra(methylenephosphonic acid) or its salts).

TABLE

| Inhibitor | Dosage (ppm) active acid | Time (hrs) | Percentage Inhibition |
|---|---|---|---|
| (I) | 25 | 2.5 | 100 |
|  |  | 8 | 92 |
|  |  | 24 | 49 |
| A | 25 | 2.5 | 64 |
|  |  | 8 | 38 |
|  |  | 24 | 24 |
| B | 25 | 2.5 | 50 |
|  |  | 8 | 23 |
|  |  | 24 | 14 |
| (I) + A | 25 | 2.5 | 100 |
|  |  | 8 | 92 |
|  |  | 24 | 50 |
| (I) + B | 25 | 2.5 | 98 |
|  |  | 8 | 81 |
|  |  | 24 | 32 |
| C | 25 | 2.5 | 51 |
| D | 25 | 2.5 | 49 |
| E | 25 | 2.5 | 34 |

The results above express the scale-inhibiting effects of the various inhibitors in terms of percentage inhibition. It is immediately apparent that the inhibitors used in the process of the invention are appreciably superior to those used for the purposes of the comparison.

I claim:

1. A method of inhibiting the precipitation and deposition of calcium oxalate scale in an aqueous system, comprising adding to said system an effective amount of a phosphonate compound represented by the general formula:

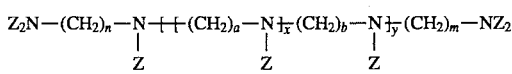

where in $Z=-CHR^1PO_3R_2$;

$R=H$, $CH_3$, $C_2H_5$ or M;

$R^1=H$, $CH_3$, $CR_3$, $C_6H_5$, or $SO_3H_2$;

M=alkali metal or ammonium ion;

$n=2-6$, $m=2-6$, $a=2-10$, $b=2-10$, $x=0-6$, and $y=1-6$, said aqueous systems having a pH from about 7–13.

2. The method of claim 1 wherein the phosphonate compound is added in an amount of from 0.5 ppm to 100 ppm.

3. The method of claim 2 wherein the phosphonate compound is added in an amount from 1 ppm to 50 ppm.

4. The method of claim 1 wherein the phosphonate compound is such that:

$n=3$; $m=3$; $b=2$ ; $x=0$; and $y=1$.

5. The method of any of the preceding claims further comprising adding, in addition to the phosphonate compound, substances selected from the group consisting of scale inhibitors, dispersants, and calcium oxalate scale formation inhibiting adjuvants.

6. The method of claim 1 wherein $n=2-4$;

$m=2-4$;

$a=2-4$;

$b=2-4$;

$x=0-3$; and $y=1-2$.

* * * * *